United States Patent [19]

Kirstgen et al.

[11] Patent Number: 5,356,931
[45] Date of Patent: Oct. 18, 1994

[54] USE OF α-ARYLACRYLIC DERIVATIVES FOR CONTROLLING PESTS

[75] Inventors: Reinhard Kirstgen, Neustadt; Rainer Otter, Laudenbach; Christoph Kuenast, Otterstadt; Uwe Kardorff, Mannhein; Wolfgang Steglich, Bonn-Roettgen; Gunda Bertram, Bonn, all of Fed. Rep. of Germany

[73] Assignee: BASF Aktiengesellschaft, Ludwigshafen, Fed. Rep. of Germany

[21] Appl. No.: 574

[22] Filed: Jan. 4, 1993

Related U.S. Application Data

[62] Division of Ser. No. 757,409, Sep. 10, 1991, abandoned.

[30] Foreign Application Priority Data

Sep. 14, 1990 [DE] Fed. Rep. of Germany ....... 4029192

[51] Int. Cl.$^5$ ............... A01N 47/10; A01N 37/10; A01N 47/40
[52] U.S. Cl. ................. 514/478; 514/479; 514/480; 514/481; 514/482; 514/483; 514/484; 514/485; 514/486; 514/487; 514/488; 514/510; 514/511; 514/514; 514/515; 514/516; 514/520; 514/521; 514/522; 514/523; 514/524; 514/525; 514/530; 514/531; 514/532; 514/533; 514/534; 514/535; 514/537; 514/538; 514/539; 514/542; 514/543; 514/544; 514/545
[58] Field of Search .......... 514/478, 482, 483, 485, 514/488, 510, 511, 514, 516, 522, 530, 531, 532, 543, 544, 479, 480, 481, 484, 486, 487, 515, 520, 521, 523, 524, 525, 533, 534, 535, 537, 538, 539, 542, 545

[56] References Cited

U.S. PATENT DOCUMENTS

| | | | |
|---|---|---|---|
| 4,723,034 | 2/1988 | Schirmer et al. | 560/60 |
| 4,782,177 | 11/1988 | Schirmer et al. | 560/60 |
| 4,857,545 | 8/1989 | Anthony et al. | 514/452 |

FOREIGN PATENT DOCUMENTS

| | | |
|---|---|---|
| 89/31625 | 5/1989 | Australia . |
| 0178826 | 4/1986 | European Pat. Off. . |
| 244077 | 11/1987 | European Pat. Off. . |
| 0256667 | 2/1988 | European Pat. Off. . |
| 2193495 | 1/1988 | United Kingdom . |

*Primary Examiner*—Richard L. Raymond
*Assistant Examiner*—John D. Pak
*Attorney, Agent, or Firm*—Keil & Weinkauf

[57] ABSTRACT

Alpha-Arylacrylic acid derivatives of the general formula I

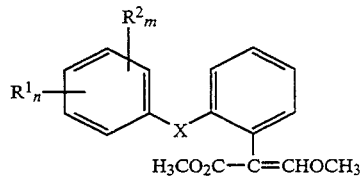

where X is ethylene or ethenylene;
n is 0 or 1;
m is 0, 1, 2, 3 or 4;
R$^1$ is cyano, cyanato, thiocyanato, nitro, hydroxyl, carboxyl, haloalkyl, haloalkoxy, unsubstituted or substituted cycloalkyl, cycloalkenyl, cycloalkadienyl, alkenyl, alkynyl or amino, alkylcarbonyl, alkoxycarbonyl, alkylaminocarbonyl, dialkylaminocarbonyl, unsubstituted or substituted benzyloxycarbonyl, benzoyl, phenylalkyl, phenylalkoxy or phenoxyalkyl,
or R$^1$ together with one of the radicals R$^2$ forms an unsubstituted or substituted 1,3-butadiene-1,4-diyl group or an unsubstituted or substituted chain consisting of carbon members and an oxygen member, and
R$^2$ is halogen, unsubstituted or substituted alkyl, alkoxy, alkenyloxy, alkynyloxy, alkadienyloxy, benzyloxy or benzylthio, are used for controlling pests.

9 Claims, No Drawings

USE OF α-ARYLACRYLIC DERIVATIVES FOR CONTROLLING PESTS

This application is a division of application Ser. No. 07/757,409, filed on Sep. 10, 1991 now abandoned.

The present invention relates to the use of α-arylacrylic acid derivatives of the general formula I

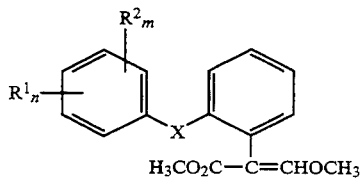

where
X is ethylene or ethenylene;
n is 0 or 1;
m is 0, 1, 2, 3 or 4, and the radicals $R^2$ may be different when m is 2, 3 or 4;
$R^1$ is cyano, cyanato, thiocyanato, nitro, hydroxyl, carboxyl, $C_1$–$C_4$-haloalkyl, $C_1$–$C_4$-haloalkoxy, $C_3$–$C_8$-cycloalkyl, $C_5$–$C_8$-cycloalkenyl or $C_5$–$C_8$-cycloalkadienyl, where these radicals may carry from one to five halogen atoms, one phenyl, phenoxy or phenylthio radical and/or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, $C_2$–$C_6$-alkenyl or $C_2$–$C_6$-alkynyl, where these radicals may carry from one to five halogen atoms, one phenyl, phenoxy or phenylthio radical and/or from one to three of the following radicals: $C_1$–$C_4$-alkoxy, $C_1$–$C_4$-haloalkoxy, $C_1$–$C_4$-alkylthio or $C_1$–$C_4$-haloalkylthio, amino which may carry one $C_1$–$C_6$-alkylcarbonyl, $C_1$–$C_6$-alkoxycarbonyl, $C_1$–$C_6$-alkylaminocarbonyl or di-$C_1$–$C_6$-alkylaminocarbonyl group and/or one or two $C_1$–$C_6$-alkyl groups, $C_1$–$C_6$-alkylcarbonyl, $C_1$–$C_6$-alkoxycarbonyl, $C_1$–$C_6$-alkylaminocarbonyl, di-$C_1$–$C_6$-alkylaminocarbonyl, benzyloxycarbonyl, benzoyl, phenyl-$C_1$–$C_4$-alkyl, phenyl-$C_1$–$C_4$-alkoxy or phenoxy-$C_1$–$C_4$-alkyl, where the aromatic radicals may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, or $R^1$ together with one of the radicals $R^2$ in the ortho-position may form a 1,3-butadiene-1,4-diyl group, where this radical may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_4$–$C_4$-haloalkylthio, or a three-membered or four-membered chain consisting of carbon members and an oxygen member, where this chain may carry from one to three $C_1$–$C_4$-alkyl groups, and $R^2$ is halogen, $C_1$–$C_{10}$-alkyl, $C_1$–$C_6$-alkoxy, $C_2$–$C_6$-alkenyloxy, $C_2$–$C_6$-alkynyloxy or $C_5$–$C_{10}$-alkadienyloxy, where these radicals may carry from one to five halogen atoms, one phenyl, phenoxy or phenylthio radical and/or from one to three of the following radicals: $C_1$–$C_4$-alkoxy, $C_1$–$C_4$-haloalkoxy, $C_1$–$C_4$-alkylthio or $C_1$–$C_4$-haloalkylthio, benzyloxy or benzylthio, where the aromatic radicals may carry from one to five halogen atoms, one phenyl, phenoxy or phenylthio radical and/or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio,
for controlling pests.

The present invention furthermore relates to a method for controlling pests.

The literature discloses alpha-arylacrylic acid derivatives as fungicides, the general formula of which embraces the compounds of the formula I which are defined at the outset (EP-A 203 606 and EP-A 229 974). α-Arylacrylic acid derivatives are also disclosed as insecticides and fungicides (EP-A 178 826) and as insecticides (EP-A 256 667 and EP-A 335 519).

It is an object of the present invention to provide novel effective possibilities for pest control.

We have found that this object is achieved and that the α-arylacrylic acid derivatives I defined at the outset are suitable for controlling pests.

The preparation of the α-arylacrylic acid derivatives is described in the literature cited at the outset (EP-A 203 606 and EP-A 229 974).

In view of the intended use of the compounds I for controlling pests, suitable substituents and indices are the following:
X is ethylene (—$CH_2$—$CH_2$—) or ethenylene (—CH=CH—);
n is 0 or 1;
m is 0, 1, 2, 3 or 4, and the radicals $R^2$ may be different when m is 2, 3 or 4;
$R^1$ is cyano, cyanato, thiocyanato, nitro, hydroxyl, carboxyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trichloromethyl, difluoromethyl or 2,2-difluoroethyl, in particular trifluoromethyl or 2,2,2-trifluoroethyl, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably dichloromethoxy, trifluoromethoxy, dichlorofluoromethoxy or pentafluoroethoxy, in particular difluoromethoxy, 2,2-difluoroethoxy or 2,2,2-trifluoroethoxy, $C_3$–$C_8$-cycloalkyl, such as cyclopropyl, cyclobutyl, cyclopentyl, cyclohexyl, cycloheptyl or cyclooctyl, preferably cycloheptyl, in particular cyclopropyl, cyclopentyl or cyclohexyl, $C_5$–$C_8$-cycloalkenyl, such as cyclopent-1-enyl, cyclopent-2-enyl, cyclopent-3-enyl, cyclhex-1-enyl, cyclohex-2-enyl, cyclohex-3-enyl, cyclohept-1-enyl, cyclohept-2-enyl, cyclohept-3-enyl, cyclohept-4-enyl, cycloct-1-enyl, cycloct-2-enyl, cycloct-3-enyl or cyclooct-1-enyl, preferably cyclopent-3-enyl or cyclohept-3-enyl, in particular cyclopent-1-enyl, cyclopent-2-enyl, cyclohex-1-enyl or cyclohex-2-enyl, or $C_5$-$C_8$-cycloalkadienyl, such as cyclopenta-1,3-dien-1-yl, cyclopenta-1,3-dien-2-yl, cyclopenta-1,3-dien-5-yl, cyclohexa-1,3-dien-1-yl, cyclohexa-1,3-dien-2-yl, cyclohexa-1,3-dien-5-yl, cyclohexa-1,4-dien-1-yl, cyclohexa-1,4-dien-3-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl, cyclohepta-1,4-dien-6-yl, cycloocta-1,3-dien-1-yl, cycloocta-1,3-dien-2-yl, cycloocta-1,3-dien-5-yl, cycloocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,4-dien-1-yl or cycloocta-1,4-dien-3-yl, preferably cyclopenta-1,3-dien-1-yl or cyclohexa-1,3-dien-2-yl, in particular cyclopenta-1,3-dien-5-yl or cyclohexa-1,3-dien-1-yl, where these cyclic radicals may carry from one to five halogen atoms, such as fluorine, chlorine, bromine or iodine, preferably fluorine, chlorine or bromine, one phenyl, phenoxy or phenylthio radical and/or from one to three of the following radicals: $C_1$-$C_4$-alkyl, such as methyl, ethyl, propyl, 1-methylethyl, butyl, 1-methylpropyl, 2-methylpropyl or 1,1-dimethylethyl, preferably ethyl, in particular methyl, $C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or 2,2,2-trifluoroethyl, in particular trifluoromethyl, $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably ethoxy, 1-methylethoxy or 1,1-dimethylethoxy, in particular methoxy, $C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro2,2-difluoroethoxy, 2,2-dichloro-2-fluoroethoxy, 2,2,2-trichloroethoxy or pentafluoroethoxy, preferably fluoromethoxy or difluoromethoxy, in particular trifluoromethoxy or 2,2-difluoroethoxy, $C_1$-$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, 1-methylethylthio or 1,1-dimethylethylthio, in particular methylthio, or $C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or fluoromethylthio, in particular difluoromethylthio or 2,2-difluoroethylthio, $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, preferably 1-methyl-1-propenyl, 1-methyl-1-butenyl, 1-ethyl-1-propenyl, 1-hexenyl, 2-hexenyl, 1-ethyl-1-butenyl or 1,1,2-trimethyl-2-propenyl, in particular ethenyl, 2-propenyl or 1-methyl-2-propenyl, or $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, preferably 2-butynyl, 1-methyl-2-propynyl or 2,2-dimethyl-3-butynyl, in particular ethynyl or 1-propynyl, where these radicals may carry from one to five halogen atoms, such as fluorine, chlorine, bromine or iodine, preferably bromine, in particular fluorine or chlorine, one phenyl, phenoxy or phenylthio radical and/or from one to three of the following radicals: $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably 1-methylethoxy, in particular methoxy, $C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably 2,2-difluoroethoxy, in particular difluoromethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably 1-methylethylthio, in particular methylthio, or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or 2,2-difluoroethylthio, in particular difluoromethylthio, amino which may carry one $C_1$–$C_6$-alkylcarbonyl group, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably ethylcarbonyl or 1-methylethylcarbonyl, in particular methylcarbonyl and 1,1-dimethylethylcarbonyl, one $C_1$–$C_6$-alkoxycarbonyl group, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 1-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropylcarbonyl, 1,2,2-trimethylpropoxycarbonyl, 1-ethyl-1-methylpropoxycarbonyl or 1-ethyl-2-methylpropoxycarbonyl, preferably 1,1-dimethylethoxycarbonyl, in particular ethoxycarbonyl, one $C_1$–$C_6$-alkylaminocarbonyl group, such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, preferably ethylaminocarbonyl or 1-methylethylaminocarbonyl, in particular methylaminocarbonyl, or one di-$C_1$–$C_6$-alkylaminocarbonyl group, in particular di-$C_1$–$C_4$-alkylaminocarbonyl, such as N,N-dimethylaminocarbonyl, N,N-diethylaminocarbonyl, N,N-dipropylaminocarbonyl, N,N-di-(1-methylethyl)-aminocarbonyl, N,N-dibutylaminocarbonyl, N,N-di-(1-methylpropyl)-aminocarbonyl, N,N-di-(2-methylpropyl)-aminocarbonyl, N,N-di-(1,1-dimethylethyl)-aminocarbonyl, N-ethyl-N-methylaminocarbonyl, N-methyl-N-propylaminocarbonyl, N-methyl-N-(1-methylethyl)-aminocarbonyl, N-butyl-N-methylaminocarbonyl, N-methyl-N-(1-methylpropyl)-aminocarbonyl, N-methyl-N-(2-methylpropyl)-aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)-aminocarbonyl, N-ethyl-N-(2-methylpropyl)-aminocarbonyl, N-ethyl-N-(1,1-dimethylethyl)-aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)-aminocarbonyl, N-(1-methylethyl)-N-(1-methylpropyl)-aminocarbonyl, N-(1-methylethyl)-N-(2-methylpropyl)-aminocarbonyl, N-(1,1-dimethylethyl)-N-(1-methylethyl)-aminocarbonyl, N-butyl-N-(1-methylpropyl)-aminocarbonyl, N-butyl-N-(2-methylpropyl)-aminocarbonyl, N-butyl-N-(1,1-dimethylethyl)-aminocarbonyl, N-(1-methylpropyl)-N-(2-methylpropyl)-aminocarbonyl, N-(1,1-dimethylethyl)-N-(1-methylpropyl)-aminocarbonyl or N-(1,1-dimethylethyl)-N-(2-methylpropyl)-aminocarbonyl, preferably N,N-diethylaminocarbonyl, N-ethyl-N-methylaminocarbonyl or N-methyl-N-(2-methyl-propyl)-aminocarbonyl, in particular N,N-dimethylaminocarbonyl, and/or one or two $C_1$–$C_6$-alkyl groups, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, $C_1$–$C_6$-alkoxycarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably ethylcarbonyl, 1-methylethylcarbonyl, in particular methylcarbonyl or 1,1-dimethylethylcarbonyl, $C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1.1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-1 -ethyl-2-methylpropoxycarbonyl, preferably 1,1-dimethylethoxycarbonyl, in particular ethoxycarbonyl, $C_1$–$C_6$-alkylaminocarbonyl, such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, preferably ethylaminocarbonyl or 1-methylethylaminocarbonyl, in particular methylaminocarbonyl, di-$C_1$–$C_6$-alkylaminocarbonyl, in particular di-$C_1$–$C_6$-alkylaminocarbonyl, such as N,N-dimethylaminocarbonyl, N,N-diethylaminocarbonyl, N,N-dipropylaminocarbonyl, N,N-di-(1-methylethyl)-aminocarbonyl, N,N-dibutylaminocarbonyl, N,N-di-(1-methylpropyl)-aminocarbonyl, N,N-di-(2-methylpropyl)-aminocarbonyl, N,N-di-(1,1-dimethylethyl)-aminocarbonyl, N-ethyl-N-methylaminocarbonyl, N-methyl-N-propylaminocarbonyl, N-methyl-N-(1-methylethyl)-aminocarbonyl, N-butyl-N-methylaminocarbonyl, N-methyl-N-(1-methylpropyl)-aminocarbonyl, N-methyl-N-(2-methylpropyl)-aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)-aminocarbonyl, N-ethyl-N-(2-methylpropyl)-aminocarbonyl, N-ethyl-N-(1,1-dimethylethyl)-aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)-aminocarbonyl, N-(1-methylethyl)-N-(1-methylpropyl)-aminocarbonyl, N(1-methylethyl)-N-(2-methylpropyl)-aminocarbonyl, N-(1,1-dimethylethyl)-N-(1-methylethyl)-aminocarbonyl, N-butyl-N-(1-methylpropyl)-aminocarbonyl, N-butyl-N-(2-methylpropyl)-aminocarbonyl, N-butyl-N-(1,1-dimethylethyl)-aminocarbonyl, N-(1-methylpropyl)-N-(2-methylpropyl)-aminocarbonyl, N-(1,1-dimethylethyl)-N-(1-methylpropyl)-aminocarbonyl or N-(1,1-dimethylethyl)-N-(2-methylpropyl)-aminocarbonyl, preferably N-ethyl-N-methylaminocarbonyl or N-methyl-N-(2-methylpropyl)-aminocarbonyl, in particular N,N-dimethylaminocarbonyl or N,N,-diethylaminocarbonyl, benzyloxycarbonyl, benzoyl, phenyl-$C_1$–$C_4$-alkyl, such as phenylmethyl, 1-phenylethyl, 2-phenylethyl, 1-phenylpropyl, 2-phenylpropyl, 3-phenylpropyl, 1-phenyl-1-methylethyl, 2-phenyl-1-methylethyl, 1-phenylbutyl, 2-phenylbutyl, 3-phenylbutyl, 4-phenylbutyl, 1-phenyl-1-methylpropyl, 1-phenyl-2-methylpropyl, 2-phenyl-1-methylpropyl, 2-phenyl-2-methylpropyl, 3-phenyl-1-methylpropyl, 3-phenyl-2-methylpropyl or 1,1-dimethyl-2-phenylethyl, preferably 2-phenylethyl, in particular phenylmethyl, phenyl-$C_1$–$C_4$-alkoxy, such as phenylmethoxy, 1-phenylethoxy, 2-phenylethoxy, 1-phenylpropoxy, 2-phenylpropoxy, 3-phenylpropoxy, 1-phenyl-1-methylethoxy, 2-phenyl-1-methylethoxy, 1-phenylbutoxy, 2-phenylbutoxy, 3-phenylbutoxy, 4-phenylbutoxy, 1-phenyl-1-methoxypropoxy, 1phenyl1-2-methylpropoxy, 2-phenyl-1-methylpropoxy, 2-phenyl- 2-methylpropoxy, 3-phenyl-1-methylpropoxy, 3-phenyl-2-methylpropoxy or 1,1-dimethyl-2-phenylethoxy, preferably 2-phenylethoxy or 1-phenyl-1-methylethoxy, in particular phenylmethoxy, or phenoxy-$C_1$-$C_4$-alkyl, such as phenoxymethyl, 1-phenoxyethyl, 2-phenoxyethyl, 1-phenoxypropyl, 2-phenoxypropyl, 3-phenoxypropyl, 1-phenoxy-1-methylethyl, 2-phenoxy-1-methylethyl, 1-phenoxybutyl, 2-phenoxybutyl, 3-phenoxybutyl, 4-phenoxybutyl, 1-phenoxy-1-methylpropyl, 1-phenoxy-2-methylpropyl, 2-phenoxy-1-methylpropyl, 2-phenoxy-2-methylpropyl, 3-phenoxy-1-methylpropyl, 3-phenoxy-2-methylpropyl or 1,1-dimethyl-2-phenoxyethyl, preferably 1-phenoxy-1-methylethyl, in particular phenoxymethyl, where the aromatic radicals may carry from one to five halogen atoms, such as fluorine, chlorine, bromine or iodine, preferably bromine, in particular fluorine or chlorine, and/or from one to three of the following radicals: $C_1$-$C_4$-alkyl, such as methyl, ethyl, propyl, 1-methylethyl, butyl, 1-methylpropyl, 2-methylpropyl or 1,1-dimethylethyl, preferably ethyl, 1-methylethyl or 1,1-dimethylethyl, in particular methyl, $C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or 2,2,2-trifluoroethyl, in particular trifluoromethyl, $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably ethoxy, 1-methylethoxy or 1,1dimethylethoxy, in particular methoxy, $C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably fluoromethoxy or difluoromethoxy, in particular trifluoromethoxy, $C_1$-$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, 1-methylethylthio or 1,1-dimethylethylthio, in particular methylthio, or $C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2 -fluoroethylthio, 2,2 -difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or fluoromethylthio, in particular difluoromethylthio or 2,2-difluoroethylthio, or $R^1$ together with one of the radicals $R^2$ in the ortho-position forms a 1,3-butadiene-1,4-diyl, where this radical may carry from one to four halogen atoms, such as fluorine, chlorine, bromine or iodine, preferably bromine, in particular fluorine or chlorine, and/or one or two of the following radicals: $C_1$-$C_4$-alkyl, such as methyl, ethyl, propyl, 1-methylethyl, butyl, 1-methylpropyl, 2-methylpropyl or 1,1-dimethylethyl, preferably ethyl, 1-methylethyl or 1,1-dimethylethyl, in particular methyl, $C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or 2,2,2-trifluoroethyl, in particular trifluoromethyl, $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably ethoxy, 1-methylethoxy or 1,1-dimethylethoxy, in particular methoxy, $C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro2,2-difluoroethoxy, 2,2-dichloro-2-fluoroethoxy, 2,2,2-trichloroethoxy or pentafluoroethoxy, preferably fluoromethoxy or difluoromethoxy, in particular trifluoromethoxy, $C_1$-$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, 1-methylethylthio or 1,1-dimethylethylthio, in particular methylthio, or $C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or fluoromethylthio, in particular difluoromethylthio or 2,2-difluoroethylthio;

or a three-membered or a four-membered chain consisting of carbon members and an oxygen member, such as oxyethyl, methoxymethyl, oxypropyl or methoxyethyl, preferably oxyethyl, where this chain may carry from one to three $C_1$-$C_4$-alkyl groups, such as methyl, ethyl, propyl, 1-methylethyl, butyl, 1-methylpropyl, 2-methylpropyl or 1,1-dimethylethyl, preferably ethyl, in particular methyl;

$R^2$ is halogen, such as fluorine, chlorine, bromine or iodine, preferably bromine, in particular fluorine or chlorine, $C_1$-$C_{10}$-alkyl, in particular $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl;

$C_1$–$C_6$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably ethoxy, 1-methylethoxy or 2,2-dimethylbutoxy, in particular methoxy, 2-methylpropoxy or 1,1-dimethylethoxy;

$C_2$–$C_6$-alkenyloxy, such as ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy or 1-ethyl-2-methyl-2-propenyloxy, preferably ethenyloxy, 1-methylethenyloxy, 3-methyl-2-butenyloxy or 3-methyl-3-butenyloxy, in particular 2-propenyloxy or 1-methyl-2-propenyloxy, $C_2$–$C_6$-alkynyloxy, such as ethynyloxy, 1-propynyloxy, 2-propynyloxy, 1-butynyloxy, 2-butynyloxy, 3-butynyloxy, 1methyl-2-propynyloxy, 1-pentynyloxy, 2-pentynyloxy, 3-pentynyloxy, 4-pentynyloxy, 1-methyl-2-butynyloxy, 1-methyl-3-butynyloxy, 2-methyl-3-butynyloxy, 3-methyl-1butynyloxy, 1,1-dimethyl-2-propynyloxy, 1-ethyl-2-propynyloxy, 1-hexynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-1-pentynyloxy, 3-methyl-4-pentynyloxy, 4-methyl-1-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 3,3-dimethyl-1-butynyloxy, 1-ethyl-2-butynyloxy, 1-ethyl-3-butynyloxy, 2-ethyl-3-butynyloxy or 1-ethyl-1-methyl-2-propynyloxy, or $C_5$–$C_{10}$-alkadienyloxy, such as 3,7-dimethyl-2,6-octadienyloxy, 3,7-dimethyl-3,7-octadienyloxy, 3,7-dimethyl-2,7-octadienyloxy or 3,7-dimethyl-3,6-octadienyloxy, where these radicals may carry from one to five halogen atoms, such as fluorine, chlorine, bromine or iodine, preferably bromine, in particular fluorine or chlorine, one phenyl, phenoxy or phenylthio radical and/or from one to three of the following radicals: $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably ethoxy, 1-methylethoxy or 1,1-dimethylethoxy, in particular methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably fluoromethoxy or difluoromethoxy, in particular trifluoromethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, 1-methylethylthio or 1,1-dimethylethylthio, in particular methylthio, or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or fluoromethylthio, in particular difluoromethylthio or 2,2-difluoroethylthio, benzyloxy or benzylthio, where the aromatic radicals may carry from one to five halogen atoms, such as fluorine, chlorine, bromine or iodine, preferably bromine, in particular fluorine or chlorine, one phenyl, phenoxy or phenylthio radical and/or from one to three of the following radicals: $C_1$–$C_4$-alkyl, such as methyl, ethyl, propyl, 1-methylethyl, butyl, 1-methylpropyl, 2-methylpropyl or 1,1-dimethylethyl, preferably ethyl, 1-methylethyl or 1,1-dimethylethyl, in particular methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or 2,2,2-trifluoroethyl, in particular trifluoromethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably ethoxy, 1-methylethoxy or 1,1-dimethylethoxy, in particular methoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably fluoromethoxy or difluoromethoxy, in particular trifluoromethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably ethylthio, 1-methylethylthio or 1,1-dimethylethylthio, in particular methylthio, or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio or fluoromethylthio, in particular difluoromethylthio or 2,2-difluoroethylthio.

The compounds of the formula I may of course be obtained both in the form of pure structural isomers and in the form of isomer pairs (enantiomers and diastereomers) or in the form of isomer mixtures, depending on the starting materials used and on the reaction conditions, and can be used as such as active ingredients.

Isomer mixtures or isomer pairs can be separated into the sterically pure components in a conventional manner. The biological activity is dependent on the steric configuration of the compounds in specific cases.

In view of their use for pest control, particularly preferred alpha-arylacrylic acid derivatives of the formula I are those in which the substituents and indices have the following meanings:

X is ethenylene, n is 0 or 1, m is 0, 1, 2 or 3, and the radicals $R^2$ may be different when m is 2 or 3, $R^1$ is cyano, $C_3$–$C_8$-cycloalkyl, $C_5$–$C_8$cycloalkenyl or $C_5$–$C_8$-cycloalkadienyl, as stated above in general and in particular, where these may carry from one to five halogen atoms as stated above in general and in particular, one phenyl, phenoxy or phenylthio radical and/or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio as stated above in general and in particular, $C_2$–$C_6$-alkenyl as stated above in general and in particular, where this radical may carry from one to five halogen atoms as stated above in general and in particular, one phenyl, phenoxy or phenylthio radical and/or from one to three of the following radicals: $C_1$–$C_4$-alkoxy, $C_1$–$C_4$-haloalkoxy, $C_1$–$C_4$-alkylthio or $C_1$–$C_4$-haloalkylthio as stated above in general and in particular, and $R^2$ is halogen as stated above in general and in particular, $C_1$–$C_4$-alkyl, $C_1$–$C_6$-alkoxy, $C_2$–$C_6$-alkenyloxy or $C_5$–$C_{10}$-alkadienyloxy, as stated above in general and in particular, where these radicals may carry from one to five halogen atoms as stated above in general and in particular, one phenyl, phenoxy or phenylthio radical and/or from one to three of the following radicals: $C_1$–$C_4$-alkoxy, $C_1$–$C_4$-haloalkoxy, $C_1$–$C_4$-alkylthio or $C_1$–$C_4$-haloalkylthio as stated above in general and in particular.

Examples of particularly preferred α-arylacrylic acid derivatives of the general formulae IA and IB are shown in Tables A and B below.

TABLE A

IA ($R = R^1 + R^2$; $x = n + m$)

| $R_x$ |
| --- |
| 2-F |
| 3-F |
| 4-F |
| 2,3-$F_2$ |
| 2,4-$F_2$ |
| 2,5-$F_2$ |
| 2,6-$F_2$ |
| 3,4-$F_2$ |
| 3,5-$F_2$ |
| 2-Cl |
| 3-Cl |
| 4-Cl |
| 2,3-$Cl_2$ |
| 2,4-$Cl_2$ |
| 2,5-$Cl_2$ |
| 2,6-$Cl_2$ |
| 3,4-$Cl_2$ |
| 3,5-$Cl_2$ |
| 2-Br |
| 3-Br |
| 4-Br |
| 2,3-$Br_2$ |
| 2,4-$Br_2$ |
| 2,5-$Br_2$ |
| 2,6-$Br_2$ |
| 3,4-$Br_2$ |
| 3,5-$Br_2$ |
| 2-Cl, 6-F |
| 3-Cl, 4-F |
| 3-Cl, 2-F |
| 2,3,4-$Cl_3$ |
| 2,3,6-$Cl_3$ |
| 3,5-$Br_2$, 2-$OCH_3$ |
| 3,5-$Br_2$, 2-$OC_2H_5$ |
| 3,5-$Br_2$, 2-$O$-i-$C_3H_7$ |
| 3-Br, 4-$OCH_3$ |
| 3-Br, 2-$OCH_3$ |
| 3-Br, 4,5-$(OCH_3)_2$ |
| 2-$OCH_3$ |
| 3-$OCH_3$ |
| 4-$OCH_3$ |
| 3,4-$(OCH_3)_2$ |
| 3,5-$(OCH_3)_2$ |
| 3,4,5-$(OCH_3)_3$ |

TABLE A-continued

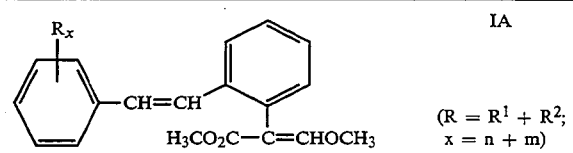

IA (R = R¹ + R²;
x = n + m)

$R_x$

2-OCH₃, 3-OC₂H₅
2,4,5-(OCH₃)₃
2-OC₂H₅
3-OC₂H₅
4-OC₂H₅
3-OC₂H₅, 4-OCH₃
3-OC₂H₅, 4-O-i-C₃H₇
3-OC₂H₅, 4-O-t-C₄H₉
3,5-(OC₂H₅)₂
3-O-i-C₃H₇
4-O-i-C₃H₇
3-O-t-C₄H₉
4-O-t-C₄H₉
4-O-i-C₄H₉
3-O-i-C₄H₉
3,4-(O-t-C₄H₉)₂
3,5-(O-t-C₄H₉)₂, 4-OCH₃

3,4-(O—\/=\/—)₂

3,4-(O—\/\/=\/—)₂

4-O—\/\/=\/

4-O—\/=\/\/=\/

3,4-(O—\/=\/\/=\/—)₂

3-OCH₂C₆H₅
4-OCH₂C₆H₅
2-OCH₂C₆H₅, 3-OCH₃
3-OCH₂C₆H₅, 4-OCH₃
4-OCH₂C₆H₅, 3-OCH₃
3,4-(OCH₂C₆H₅)₂
3-OCHF₂
4-OCHF₂
2-OCF₂CHF₂
3-OCF₂CHF₂
4-OCF₂CHF₂
3-CF₃
4-CF₃
2-CH₃
3-CH₃
4-CH₃
2,4-(CH₃)₂
3,4-(CH₃)₂
3-C₂H₅
4-C₂H₅
3-t-C₄H₉
4-t-C₄H₉
3-t-C₄H₉, 4-OCH₃
3,5-(t-C₄H₉)₂, 4-OCH₃
3-CH₃, 4-OCH₃
3,4-(t-C₄H₉)₂
2,3-CH=CH—CH=CH
3,4-CH=CH—CH=CH
3-Cyclopentenyl, 2-CH₃
3-Cyclohexenyl, 2-CH₃
3-Cycloheptenyl, 2-CH₃
3-(2-Norbornen-2-yl), 2-CH₃
3-Cyclohexenyl, 2-CH₃, 5-F
3-Cyclopentenyl, 2-CH₃, 6-Cl 3-(1,3-Cyclohexadienyl), 2-CH₃
3-Cyclopropyl, 2-CH₃
3-Norbornen-2-yl, 2-CH₃
3-i-C₃H₇, 2-CH₃
3-CH(C₂H₅)₂, 2-CH₃
3-CH(CH₃)(n-C₃H₇), 2-CH₃
3-s-C₄H₉, 2-CH₃
3-n-C₄H₉, 2-CH₃
3-CH(i-C₃H₇)₂, 2-CH₃
3-CH(CH₃)(n-C₃H₇), 2-CH₃
3-C(CH₃)=CH₂, 2-CH₃
3-C(C₂H₅)=CH₂, 2-CH₃
3-CH=CH₂, 2-CH₃
3-C(CH₃)=CHCH₃, 2-CH₃
3-C(CH₂CH₃)=CHCH₃, 2-CH₃
3-CH₃, 2-Cl
3-C₂H₅, 2-Cl
3-i-C₃H₇,
3-t-C₄H₉, 2-Cl
3-s-C₄H₉, 2-Cl
3-Cyclopentyl, 2-Cl
3-Cyclohexyl, 2-Cl
3-Cycloheptyl, 2-Cl
3-Norborn-2-yl, 2-Cl
3-(2-Cyclopentyl), 2-Cl
3-(2-Cyclohexenyl), 2-Cl
3-C(CH₃)=CHCH₃, 2-Cl
3-CH(CH₃)CH=CH₂, 2-Cl
3-CH₃, 2-F
3-C₂H₅, 2-F
3-i-C₃H₇, 2-F
3-s-C₄H₉, 2-F
3-t-C₄H₉, 2-F
3-CH(C₂H₅)₂, 2-F
3-Cyclopropyl, 2-F
3-Cyclopentyl, 2-F
3-Cyclohexyl, 2-F
3-(2-Cyclohexenyl), 2-F
3-(Norborn-2-yl), 2-F
3-C(CH₃)=CH₂, 2-F
3-CH₃, 2-Br
C-i-C₃H₇, 2-Br
3-t-C₄H₉, 2-Br
3-Cyclopropyl, 2-Br
3-Cyclopentyl, 2-Br
3-Cyclohexyl, 2-Br
3-CH₃, 2-OCH₃
3-i-C₃H₇, 2-OCH₃
3-t-C₄H₉, 2-OCH₃
3-Cyclopropyl, 2-OCH₃
3-Cyclopentyl, 2-OCH₃
3-Cyclohexyl, 2-OCH₃
3-CN
4-CN
4-SCN
3-NO₂
4-NO₂
3-NO₂, 4-CH₃
3-NO₂, 4-Cl
3-N(CH₃)₂
4-N(CH₃)₂
3-NHCOCH₃
3-NHCO₂CH₃
4-NHCO₂CH₃
4-NHCON(CH₃)₂
3-CO₂CH₃
3-CO₂C₂H₅
3-CO₂-i-C₃H₇
3-CO₂-t-C₄H₉
4-CO₂CH₃
4-CO₂C₂H₅
4-CO₂-i-C₃H₇
4-CO₂-t-C₄H₉H

TABLE A-continued

Structure IA: Ar-CH=CH-Ar' where Ar = phenyl with $R_x$ substituents, Ar' = ortho-substituted phenyl with $H_3CO_2C-C=CHOCH_3$ group.

(R = R$^1$ + R$^2$; x = n + m)

| $R_x$ |
|---|
| 3-CO$_2$CH$_2$C$_6$H$_5$ |
| 4-CO$_2$CH$_2$C$_6$H$_5$ |
| 3-Benzoyl |
| 4-Benzoyl |
| 4-CONHCH$_3$ |
| 3-CONHCH$_3$ |
| 3-CON(CH$_3$)$_2$ |
| 3-Phenethyl |
| 4-Phenethyl |
| 3-Phenethyloxy |
| 4-Phenethyloxy |
| 3-Phenoxymethyl |
| 4-Phenoxyethyl |
| 3,4-OC(CH$_3$)$_2$CH$_2$ |
| 4-OCH$_2$CH(C$_2$H$_5$)(n-C$_4$H$_9$) |

TABLE B

Structure IB: Ar-CH$_2$-CH$_2$-Ar' where Ar = phenyl with $R_x$ substituents, Ar' = ortho-substituted phenyl with $H_3CO_2C-C=CHOCH_3$ group.

(R = R$^1$ + R$^2$; x = n + m)

| $R_x$ |
|---|
| 2-F, |
| 3-F, |
| 4-F, |
| 2,3-F$_2$ |
| 2,4-F$_2$ |
| 2,5-F$_2$ |
| 2,6-F$_2$ |
| 3,4-F$_2$ |
| 3,5-F$_2$ |
| 2-Cl |
| 3-Cl |
| 4-Cl |
| 2,3-Cl$_2$ |
| 2,4-Cl$_2$ |
| 2,5-Cl$_2$ |
| 2,6-Cl$_2$ |
| 3,4-Cl$_2$ |
| 3,5-Cl$_2$ |
| 2-Br |
| 3-Br |
| 4-Br |
| 2,3-Br$_2$ |
| 2,4-Br$_2$ |
| 2,5-Br$_2$ |
| 2,6-Br$_2$ |
| 3,4-Br$_2$ |
| 3,5-Br$_2$ |
| 2-Cl, 6-F |
| 3-Cl, 4-F |
| 3-Cl, 2-F |
| 2,3,4-Cl$_3$ |
| 2,3,6-Cl$_3$ |
| 3,5-Br$_2$, 2-OCH$_3$ |
| 3,5-Br$_2$, 2-OC$_2$H$_5$ |
| 3,5-Br$_2$, 2-O-i-C$_3$H$_7$ |
| 3-Br, 4-OCH$_3$ |
| 3-Br, 2-OCH$_3$ |
| 3-Br, 4,5-(OCH$_3$)$_2$ |
| 2-OCH$_3$ |
| 3-OCH$_3$ |
| 4-OCH$_3$ |
| 3,4-(OCH$_3$)$_2$ |
| 3,5-(OCH$_3$)$_2$ |
| 3,4,5-(OCH$_3$)$_3$ |

TABLE B-continued

| $R_x$ |
|---|
| 2-OCH$_3$, 3-OC$_2$H$_5$ |
| 2,4,5-(OCH$_3$)$_3$ |
| 2-OC$_2$H$_5$ |
| 3-OC$_2$H$_5$ |
| 4-OC$_2$H$_5$ |
| 3-OC$_2$H$_5$, 4-OCH$_3$ |
| 3-OC$_2$H$_5$, 4-O-i-C$_3$H$_7$ |
| 3-OC$_2$H$_5$, 4-O-t-C$_4$H$_9$ |
| 3,5-(OC$_2$H$_5$)$_2$ |
| 3-O-i-C$_3$H$_7$ |
| 4-O-i-C$_3$H$_7$ |
| 3-O-t-C$_4$H$_9$ |
| 4-O-t-C$_4$H$_9$ |
| 4-O-i-C$_4$H$_9$ |
| 3-O-i-C$_4$H$_9$ |
| 3,4-(O-t-C$_4$H$_9$)$_2$ |
| 3,5-(O-t-C$_4$H$_9$)$_2$, 4-OCH$_3$ |
| 3-OCHF$_2$ |
| 4-OCHF$_2$ |
| 2-OCF$_2$CHF$_2$ |
| 3-OCF$_2$CHF$_2$ |
| 4-OCF$_2$CHF$_2$ |
| 3-CF$_3$ |
| 4-CF$_3$ |
| 2-CH$_3$ |
| 3-CH$_3$ |
| 4-CH$_3$ |
| 2,4-(CH$_3$)$_2$ |
| 3,4-(CH$_3$)$_2$ |
| 3-C$_2$H$_5$ |
| 4-C$_2$H$_5$ |
| 3-t-C$_4$H$_9$ |
| 4-t-C$_4$H$_9$ |
| 3-t-C$_4$H$_9$, 4-OCH$_3$ |
| 3,5-(t-C$_4$H$_9$)$_2$, 4-OCH$_3$ |
| 3-CH$_3$, 4-OCH$_3$ |
| 3,4-(t-C$_4$H$_9$)$_2$ |
| 2,3-CH=CH—CH=CH |
| 3,4-CH=CH—CH=CH |
| 3-Cyclopropyl, 2-CH$_3$ |
| 3-Norbornen-2-yl, 2-CH$_3$ |
| 3-i-C$_3$H$_7$, 2-CH$_3$ |
| 3-CH(C$_2$H$_5$)$_2$, 2-CH$_3$ |
| 3-CH(CH$_3$)(n-C$_3$H$_7$), 2-CH$_3$ |
| 3-s-C$_4$H$_9$, 2-CH$_3$ |
| 3-n-C$_4$H$_9$, 2-CH$_3$ |
| 3-CH(i-C$_3$H$_7$)$_2$, 2-CH$_3$ |
| 3-CH(CH$_3$)(n-C$_3$H$_7$), 2-CH$_3$ |
| 3-CH$_3$, 2-Cl |
| 3-C$_2$H$_5$, 2-Cl |
| 3-i-C$_3$H$_7$, 2-Cl |
| 3-t-C$_4$H$_9$, 2-Cl |
| 3-s-C$_4$H$_9$, 2-Cl |
| 3-Cyclopentyl, 2-Cl |
| 3-Cyclohexyl, 2-Cl |
| 3-Cycloheptyl, 2-Cl |
| 3-Norborn-2-yl, 2-Cl |
| 3-CH$_3$, 2-F |
| 3-C$_2$H$_5$, 2-F |
| 3-i-C$_3$H$_7$, 2-F |
| 3-s-C$_4$H$_9$, 2-F |
| 3-t-C$_4$H$_9$, 2-F |
| 3-CH(C$_2$H$_5$)$_2$, 2-F |
| 3-Cyclopropyl, 2-F |
| 3-Cyclopentyl, 2-F |
| 3-Cyclohexyl, 2-F |
| 3-(Norborn-2-yl), 2-F |
| 3-CH$_3$, 2-Br |
| 3-i-C$_3$H$_7$, 2-Br |
| 3-t-C$_4$H$_9$, 2-Br |
| 3-Cyclopropyl, 2-Br |
| 3-Cyclopentyl, 2-Br |
| 3-Cyclohexyl, 2-Br |

TABLE B-continued $$\text{IB}: \quad R_x\text{-}\underset{\text{(ring)}}{}\text{-CH}_2\text{-CH}_2\text{-}\underset{\text{(ring)}}{}\text{-C(H}_3\text{CO}_2\text{C)}=\text{CHOCH}_3$$

(R = R¹ + R²; x = n + m)

| $R_x$ |
|---|
| 3-CH₃, 2-OCH₃ |
| 3-i-C₃H₇, 2-OCH₃ |
| 3-t-C₄H₉, 2-OCH₃ |
| 3-Cyclopropyl, 2-OCH₃ |
| 3-Cyclopentyl, 2-OCH₃ |
| 3-Cyclohexyl, 2-OCH₃ |
| 4-SCN |
| 3-NO₂ |
| 4-NO₂ |
| 3-NO₂, 4-CH₃ |
| 3-NO₂, 4-Cl |
| 3-N(CH₃)₂ |
| 4-N(CH₃)₂ |
| 3-NHCOCH₃ |
| 3-NHCO₂CH₃ |
| 4-NHCO₂CH₃ |
| 4-NHCON(CH₃)₂ |
| 3-CO₂CH₃ |
| 3-CO₂C₂H₅ |
| 3-CO₂-i-C₃H₇ |
| 3-CO₂-t-C₄H₉ |
| 4-CO₂CH₃ |
| 4-CO₂C₂H₅ |
| 4-CO₂-i-C₃H₇ |
| 4-CO₂-t-C₄H₉ |
| 3-Benzoyl |
| 4-Benzoyl |
| 4-CONHCH₃ |
| 3-CONHCH₃ |
| 3-CON(CH₃)₂ |
| 3-Phenethyl |
| 4-Phenethyl |
| 3-Phenethyl |
| 4-Phenethyl |
| 3-Phenethyloxy |
| 4-Phenethyloxy |
| 3-Phenoxymethyl |
| 4-Phenoxyethyl |
| 3,4-OC(CH₃)₂CH₂ |
| 4-OCH₂CH(C₂H₅)(n-C₄H₉) |

The compounds of the formula I are suitable for effectively controlling pests from the class consisting of the insects, arachnida and nematodes. They can be used as pesticides in crop protection, in the hygiene and veterinary sectors and for the protection of stored materials.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Hellothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*; from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria*; from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*; from the order of the Thysanoptera, for example *Frankliniella fusca, Frankliniella occidentalis, Frankliniella tritici, Scirtothrips citri, Thrips oryzae, Thrips palmi* and *Thrips tabaci*; from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta*; from the order of the Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor*; from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulocorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri,*

*Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii*; from the order of the Isoptera, for example *Calotermes flavicollis, Leucotermes flavipes, Reticulitermes lucifugus* and *Termes natalensis*; from the order of the Orthoptera, for example *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*; from the class of the Arachnoidea, for example Acarina, such as *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotertranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanazawai, Tetranychus pacificus, Tetranychus telarius* and *Tetranychus urticae*; from the class of the nematodes, for example root gall nematodes, e.g. *Meloidogyne hapla, Meloidogyne incognita* and *Meloidogyne javanica*, cyst-forming nematodes, e.g. *Globodera rostochiensis, Heterodera avenae, Heterodera glycinae, Heterodera schatii, Hetrodera triflolii*, and stem and leaf eelworms, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be applied as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure a very fine distribution of the novel active ingredients.

Mineral oil fractions having a medium to high boiling point such as kerosene or diesel oil, and coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone and strongly polar solvents, e.g. dimethylformamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (spray powders, oil dispersions) by adding water. For the preparation of emulsions, pastes or oil dispersions, the substances as such or dissolved in an oil or solvent, can be homogenized in water by means of wetting agents, adherents, dispersants or emulsifiers. However, it is also possible to prepare concentrates which consist of active substance, wetting agents, adherents, dispersants or emulsifiers, and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensates of sulfated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active substances together with a solid carrier.

The formulations contain in general from 0.01 to 95, preferably from 0.1 to 90, % by weight of the active ingredient. The active ingredients are used in a purity of from 90 to 100%, preferably from 95 to 100% (according to NMR). Examples of formulations are:

I. 5 parts by weight of compound No. 1.001 are thoroughly mixed with 95 parts by weight of finely divided kaolin. A dusting agent which contains 5% by weight of the active ingredient is obtained in this manner.

II. 30 parts by weight of compound No. 2.013 are thoroughly mixed with a mixture of 92 parts by weight of silica gel powder and 8 parts by weight of liquid paraffin, which has been sprayed onto the surface of the silica gel. A formulation of the active ingredient having good adhesion is obtained in this manner (active ingredient content 23% by weight).

III. 10 parts by weight of compound No. 1.005 are dissolved in a mixture which consists of 90 parts by weight of xylene, 6 parts by weight of the adduct of from 8 to 10 mol of ethylene oxide with 1 mol of oleic acid N-monoethanolamide, 2 parts by weight of the calcium salt of dodecylbenzene sulfonic acid and 2 parts by weight of the adduct of 40 mol of ethylene oxide with 1 mol of castor oil (active ingredient content 9% by weight).

IV. 20 parts by weight of compound No. 1.036 are dissolved in a mixture which consists of 60 parts by weight of cyclohexanone, 30 parts by weight of isobutanol, 5 parts by weight of the adduct of 7 mol of ethylene oxide with 1 mol of isooctylphenol and 5 parts by weight of the adduct of 40 mol of ethylene oxide with 1 mol of castor oil (active ingredient content 16% by weight).

V. 80 parts by weight of compound No. 1.009 are thoroughly mixed with 3 parts by weight of the sodium salt of diisobutylnaphthalene-alpha-sulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of compound No. 2.002 are mixed with 10 parts by weight of N-methyl-α-pyrrolidone, and a solution which is suitable for use in the form of very small drops is obtained (active ingredient content 90% by weight).

VII. 20 parts by weight of compound No. 1.004 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 1.002 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate and ureas, and vegetable products, such as grain flour, bark meal, wood meal and nutshell meal, cellulosic powders and other solid carriers.

The active ingredient concentrations in the ready-to-use formulations can be varied within relatively wide ranges.

In general, they are from 0.0001 to 10%, preferably from 0.01 to 1%.

The active ingredients can also be successfully used by the ultralow volume method (ULV), and it is possible to apply formulations containing more than 95% by weight of active ingredient or even the active ingredient without additives.

The application rate of active ingredient in the field is from 0.01 to 3, preferably from 0.05 to 1, kg/ha.

Oils of various types, herbicides, fungicides, other pesticides and bactericides, can be added to the active ingredients, if necessary immediately before use (tank mix). These agents can be mixed with the novel agents in a weight ratio of from 1:10 to 10:1.

Synthesis Examples

The methods described in the Synthesis Examples below were used with appropriate modification of the starting compounds in order to obtain further compounds I. The compounds thus obtained are listed in the Tables below, together with the physical data. 2-(β-Methoxy-α-methoxycarbonylvinyl)-3'-chloro-4'fluorostilbene (Active Ingredient Example 1.015)

A solution of 9.4 g of dimethyl 2-(β-methoxy-α-methoxycarbonylvinyl)-benzylphosphonate, 5.1 g of 3-chloro-4-fluorobenzaldehyde and 100 ml of absolute tetrahydrofuran is added, at 25° C., to a suspension of 0.94 g of sodium hydride in 100 ml of absolute tetrahydrofuran. After 12 hours, the reaction mixture was added to ice water. After extraction (tert-butyl methyl ether) and chromatographic purification (silica gel, 9:1 toluene/ethyl acetate), 6.3 g of the product were obtained as a yellow oil (E/Z ratio 9:1). Methyl α-[2-(3'-chloro-4'-fluoro)-phenylethylphenyl]-β-methoxyacrylate (Active Ingredient Example 2.022)

2 g of 2-(β-methoxy-α-methoxycarbonylvinyl)-3'-chloro-4'-fluorostilbene in 100 ml of tetrahydrofuran were hydrogenated at 25° C. in the presence of 1 g of Pd/C (10% strength) with hydrogen at 0.3 bar gauge pressure. After 3 hours, the catalyst and the solvent were removed. 1.25 g of the product of melting point 70°–75° C. were obtained.

TABLE 1

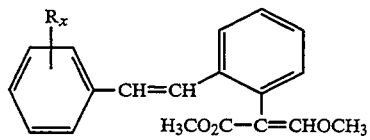

IA

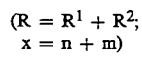

(R = R¹ + R²; x = n + m)

| No. | $R_x$ | Phys. Data (mp [°C.]; IR [cm$^{-1}$]) |
|---|---|---|
| 1.001 | 2-F | 69–70 |
| 1.002 | 3-F | 103–105 |
| 1.003 | 4-F | 137–140 |
| 1.004 | 2,4-F$_2$ | oil |
| 1.005 | 3,4-F$_2$ | 107–110 |
| 1.006 | 2-Cl | 147–148 |
| 1.007 | 3-Cl | 110–111 |
| 1.008 | 4-Cl | 113–115 |
| 1.009 | 2,4-Cl$_2$ | 134–136 |
| 1.010 | 2,6-Cl$_2$ | 127–128 |
| 1.011 | 3,4-Cl$_2$ | 96–98 |
| 1.012 | 3,5-Cl$_2$ | 144–147 |
| 1.013 | 4-Br | 138–139 |
| 1.014 | 2-Cl, 6-F | 139–140 |
| 1.015 | 3-Cl, 4-F | 1708,1632,1501,1258,1129 |
| 1.016 | 3-Br, 4-OCH$_3$ | 86–88 |
| 1.017 | 3-Br, 2-OCH$_3$ | 122 |
| 1.018 | 2-OCH$_3$ | 60–62 |

TABLE 1-continued

IA

[Structure: Ar-CH=CH-Ar' where one aryl bears Rx substituents and the other bears -C(CO2CH3)=CHOCH3 group]

(R = R¹ + R²; x = n + m)

| No. | R$_x$ | Phys. Data (mp [°C.]; IR [cm$^{-1}$]) |
|---|---|---|
| 1.019 | 3-OCH$_3$ | 102–103 |
| 1.020 | 4-OCH$_3$ | 125–127 |
| 1.021 | 3,4,5-(OCH$_3$)$_3$ | 118–121 |
| 1.022 | 3-OC$_2$H$_5$ | 88–92 |
| 1.023 | 3-OC$_2$H$_5$, 4-OCH$_3$ | 113–117 |
| 1.024 | 4-O-t-C$_4$H$_9$ | 136–137 |
| 1.025 | 4-O-i-C$_4$H$_9$ | 98 |
| 1.026 | 3,4-(O-CH$_2$-C(CH$_3$)=CH-CH$_3$)$_2$ | 78 |
| 1.027 | 3,4-(O-CH$_2$-CH$_2$-C(CH$_3$)=CH$_2$)$_2$ | 2940,1710,1630,1510,1260,1130 |
| 1.028 | 4-O-CH$_2$-CH$_2$-C(CH$_3$)=CH$_2$ | 84 |
| 1.029 | 4-O-CH$_2$-CH=C(CH$_3$)-CH$_2$-CH$_2$-CH=C(CH$_3$)$_2$ | 83 |
| 1.030 | 3,4-(O-CH$_2$-CH=C(CH$_3$)-CH$_2$-CH$_2$-CH=C(CH$_3$)$_2$)$_2$ | 67 |
| 1.031 | 3-OCH$_2$C$_6$H$_5$ | 69–70 |
| 1.032 | 3-OCH$_2$C$_6$H$_5$, 4-OCH$_3$ | 142–147 |
| 1.033 | 4-OCH$_2$C$_6$H$_5$, 3-OCH$_3$ | 117–122 |
| 1.034 | 3,4-(OCH$_2$C$_6$H$_5$)$_2$ | 109–111 |
| 1.035 | 2-OCF$_2$CHF$_2$ | 1708,1634,1259,1192,1127 |
| 1.036 | 3-OCF$_2$CHF$_2$ | 1708,1635,1258,1196,1125 |
| 1.037 | 4-OCF$_2$CHF$_2$ | 104–106 |
| 1.038 | 3-CF$_3$ | 75–77 |
| 1.039 | 4-CF$_3$ | 124–125 |
| 1.040 | 2-CH$_3$ | 156–158 |
| 1.041 | 3-CH$_3$ | 95–97 |
| 1.042 | 4-CH$_3$ | 138–139 |
| 1.043 | 2,4-(CH$_3$)$_2$ | 115–116 |
| 1.044 | 3-t-C$_4$H$_9$ | oil |
| 1.045 | 4-t-C$_4$H$_9$ | oil |
| 1.046 | 3-t-C$_4$H$_9$, 4-OCH$_3$ | 140–142 |
| 1.047 | 3,5-(t-C$_4$H$_9$)$_2$, 4-OCH$_3$ | 95–102 |
| 1.048 | 2,3-CH=CH—CH=CH | Harz |
| 1.049 | 3,4-CH=CH—CH=CH | 158–159 |
| 1.050 | 3-C(CH$_2$CH$_3$)=CHCH$_3$, 2-CH$_3$ | 1711,1633,1434,1255,1128 |
| 1.051 | 3-i-C$_3$H$_7$, 2-Cl | 1709,1633,1256,1128 |
| 1.052 | 3-Cyclopentyl, 2-Cl | 1710,1634,1256,1128 |
| 1.053 | 3-NO$_2$, 4-Cl | 168–169 |
| 1.054 | 3,4-OC(CH$_3$)$_2$CH$_2$ | 1709,1631,1499,1434,1256,1128 |
| 1.055 | 4-OCH$_2$CH(C$_2$H$_5$)(n-C$_4$H$_9$) | 88 |

TABLE 2

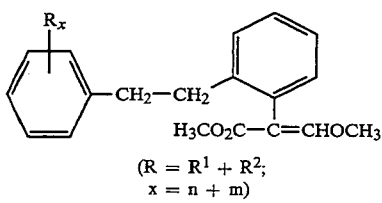

(R = R¹ + R²;
x = n + m)

| Nr.   | $R_x$                              | Phys. Data (mp [°C.]; IR [cm$^{-1}$]) |
|-------|------------------------------------|----------------------------------------|
| 2.001 | 2-F                                | 48–50                                  |
| 2.002 | 3-F                                | 46–48                                  |
| 2.003 | 4-F                                | 51–52                                  |
| 2.004 | 2-Cl                               | 69–72                                  |
| 2.005 | 3-Cl                               | 45–48                                  |
| 2.006 | 2,6-Cl$_2$                         | 119–121                                |
| 2.007 | 3,4-Cl$_2$                         | 87–89                                  |
| 2.008 | 2-OCH$_3$                          | 72–75                                  |
| 2.009 | 3-OCH$_3$                          | 26–30                                  |
| 2.010 | 3-OC$_2$H$_5$                      | 1708,1634,1443,1255,1126               |
| 2.011 | 2-OCF$_2$CHF$_2$                   | 1707,1635,1492,1195,1126               |
| 2.012 | 4-OCF$_2$CHF$_2$                   | 1707,1635,1508,1190,1125               |
| 2.013 | 3-CF$_3$                           | 48–50                                  |
| 2.014 | 4-CF$_3$                           | 72–75                                  |
| 2.015 | 4-CH$_3$                           | 46–49                                  |
| 2.016 | 3-t-C$_4$H$_9$                     | 1709,1634,1254,1127                    |
| 2.017 | 3-t-C$_4$H$_9$, 4-OCH$_3$          | 1709,1634,1496,1255,1126               |
| 2.018 | 3,5-(t-C$_4$H$_9$)$_2$, 4-OCH$_3$  | 2953,1710,1635,1257,1126               |
| 2.019 | 3,4-CH=CH—CH=CH                    | 92–93                                  |
| 2.020 | 3-CH$_3$, 2-Cl                     | 56–58                                  |
| 2.021 | 4-N(CH$_3$)$_2$                    | 76–78                                  |
| 2.022 | 3-Cl, 4-F                          | 70–75                                  |
| 2.023 | 3,4,5-Cl$_3$                       | oil                                    |
| 2.024 | 2,3-CH=CH—CH=CH                    | oil                                    |

Use Examples

The insecticidal action of the compounds of the general formula I could be demonstrated by the following experiments:

The active ingredients were prepared
a) as a 0.1% strength solution in acetone or
b) as a 10% strength solution in a mixture of 70% by weight of cyclohexanol, 20% by weight of Nekanil ® LN (Lutensol ® AP6, wetting agent having an emulsifying and dispersant action and based on ethoxylated alkylphenols) and 10% by weight of Emulphor ® EL (Emulan ® EL, emulsifier based on ethoxylated fatty alcohols) and diluted to the desired concentration with acetone in the case of a) and with water in the case of b).

After the end of the experiments, the lowest concentration, in each case, at which the compounds caused 80–100% inhibition or kill (action threshold or minimum concentration) compared with untreated control experiments was determined.

A. Musca domestica (housefly), breeding test 25 ml of a dry feed mix (1 kg of bran, 250 g of yeast powder and 35 g of fishmeal) were mixed with the active ingredient at 25 ml of a milk/sugar solution (1 l of milk and 42 g of sugar), after which 20 larvae in the first development stage (L1) were placed on said mix.

After the larvae in a controlled experiment had hatched, the kill rate was determined.

In this test, compounds 1.001, 1.002, 1.003, 1.004, 1.005, 1.006, 1.007, 1.008, 1.009, 1.011, 1.015, 1.016, 1.020, 1.023, 1.024, 1.034, 1.036, 1.037, 1.039, 1.041, 1.042, 1.043, 1.044, 1.045 and 2.012 had action thresholds of from 2 to 100 ppm.

B. Plutella maculipennis (diamondback moth), inhibition of ingestion

Young kohlrabi leaves were wet with the aqueous active ingredient formulation and then placed on a moistened filter. 10 caterpillars in the fourth stage of development were then placed on each of the prepared leaves.

After 48 hours, the inhibition of ingestion was determined.

In this test, compounds 1.001, 1.002, 1.003, 1.004, 1.005, 1.006, 1.007, 1.009, 1.011, 1.015, 1.016, 1.023, 1.031, 1.034, 1.036, 1.041, 1.043, 1.044, 1.049 and 2.004 had action thresholds of from 40 to 1,000 ppm.

C. Tetranychus telarius (red spider mite), contact action potted bushbeans which had the second pair of secondary leaves and were severely infested with mites were sprayed to run-off with aqueous active ingredient formulation.

After 5 days in a greenhouse, the success of control was determined using a binocular microscope.

In this test, compounds 1.001, 1.002, 1.004, 1,005, 1.009, 1.015, 1.034, 1.035, 1.039, 1.041, 1.044, 1.045, 1.050, 1.051, 1.052, 1.054, 2.002, 2.005, 2.013, 2.016, 2.017 and 2.020 had action thresholds of from 100 to 1,000 ppm.

We claim:

1. A method of controlling arachnids, wherein the arachnids are treated with an arachnicidally effective amount of an alpha-arylacrylic acid derivative of the formula I

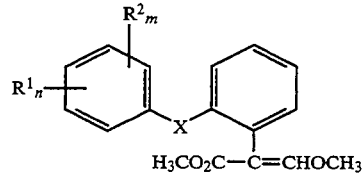

where
X is ethenylene;
n is 0 or 1;
m is 0, 1, 2, 3, or 4, and the radicals R² may be different when m is 2, 3, or 4;
R₁ is cyano, cyanato, thiocyanato, nitro hydroxyl, or carboxyl, C$_1$–C$_4$-haloalkyl, C$_1$–C$_4$ haloalkoxy, C$_3$–C$_8$-cycloalkyl, C$_5$–C$_8$-cycloalkenyl or C$_5$–C$_8$-cycloalkadienyl, where these groups may carry from one to five halogen atoms, one phenyl, phenoxy or phenylthio group or may carry from one to three of the following groups: C$_1$–C$_4$-alkyl, C$_1$–C$_4$-haloalkyl, C$_1$C$_4$-alkoxy, C$_1$–C$_4$-haloalkoxy, C$_1$–C$_4$-alkylthio or C$_1$–C$_4$-haloalkylthio; C$_2$–C$_6$-alkenyl or C$_2$–C$_6$-alkynl, where these groups may carry from one to five halogen atoms, one phenyl, phenoxy or phenylthio group or may carry from one to three of the following groups: C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio or C$_1$–C$_4$-haloalkylthio; amino which may carry one, C$_1$–C$_6$-alkylcarbonyl, C$_1$–C$_6$-alkoxycarbonyl, C$_1$–C$_6$-alkylaminocarbonyl, di-C$_1$–C$_6$-alkylaminocarbonyl; benzyloxycarbonyl, benzoyl, phenyl-C$_1$–C$_4$-alkyl, phenyl-C$_1$–C$_4$-alkoxy, or phenoxy-C$_1$–C$_4$-alkyl, where the aromatic groups may carry from one to five halogen atoms or may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

or $R^1$ together with $R^2$ in the ortho-position may form a 1, 3-butadiene-1, 4-diyl group, where this group may carry from one to four halogen atoms or may carry one or two of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; or a three-membered or four-membered chain consisting of carbon members and an oxygen member, where this chain may carry from one to three $C_1$–$C_4$-alkyl groups, and $R^2$ is halogen; $C_1$–$C_{10}$-alkyl, $C_1$–$C_6$-alkoxy, $C_2$–$C_{10}$-alkynyloxy or $C_5$–$C_{10}$-alkadienyloxy, where these groups may carry from one to five halogen atoms, one phenyl, phenoxy or phenylthio group or may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; benzyloxy or benzylthio, where the aromatic groups may carry from one to five halogen atoms, one phenyl, phenoxy or phenylthio group or may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, provided that n is not 0 when m is 0; n is not 0 when m is 1 and $R^2$ denotes halogen in 4-position of the phenyl radical or when m is 2 and R2 denotes halogen in 2- and 6-position of the phenyl group.

2. A method of controlling arachnids, according to claim 1, wherein the arachnids are treated with an arachnicidally effective amount of an alpha-arylacrylic acid derivative of the formula I

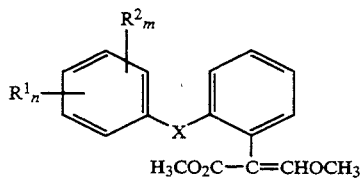

where
X is ethenylene;
n is 0 or 1;
m is 0, 1, 2, 3, or 4, and the groups $R^2$ may be different when m is 2, 3, or 4;
$R^1$ is cyano, $C_3$–$C_8$-cycloalkyl, $C_5$–$C_8$-cycloalkenyl or $C_5$–$C_8$-cycloalkadienyl, where these groups may carry from one to five halogen atoms, one phenyl, phenoxy or phenylthio group or from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio, or $C_2$–$C_6$-alkenyl, where this group may carry from one to five halogen atoms, one phenyl, phenoxy or phenylthio or may carry form one to three of the following groups: $C_1$–$C_4$-alkoxy, $C_1$–$C_4$-haloalkoxy, $C_1$–$C_4$-alkylthio or $C_1$–$C_4$-haloalkylthio, and $R^2$ is halogen; $C_1$–$C_4$-alkyl, $C_1$–$C_4$-alkoxy, $C_2$–$C_4$-alkynyloxy or $C_5$–$C_{10}$-alkadienyloxy, where these groups may carry from one to five halogen atoms, one phenyl, phenoxy or phenylthio group or may carry from one to three of the following groups: $C_1$–$C_4$-alkoxy, $C_1$–$C_4$-haloalkoxy, $C_1$–$C_4$-alkylthio or $C_1$–$C_4$-haloalkylthio, provided that n is not 0 when m is 0; n is not 0 when m is 1 and $R^2$ denotes halogen in 4-position of the phenyl radical or when m is 2 and $R^2$ denotes halogen in 2- and 6-position of the phenyl group.

3. A method of controlling arachnids, according to claim 1, wherein the arachnids are treated with an arachnicidally effective amount of an alpha-arylacrylic acid derivative of the formula I

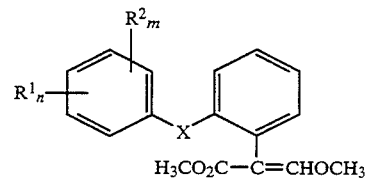

where
X is ethenylene;
n is 0 or 1;
m is 0, 1, 2, 3, or 4, and the radicals $R^2$ may be different when m is 2, 3, or 4;
$R^1$ is cyano, nitro, $C_1$–$C_4$-haloalkyl, $C_1$–$C_4$-haloalkoxy, $C_3$–$C_8$-cycloalkyl, $C_2$–$C_6$-alkenyl or $C_2$–$C_6$-alkenyl, or $R^1$ together with $R^2$ in the ortho-position may form a 1, 3-butadiene-1, 4-diyl-group, where this group may carry from one to four halogen atoms or may carry one or two of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; or a three-membered or four-membered chain consisting of carbon members and an oxygen member, where this chain may carry form one to three $C_1$–$C_4$-alkyl groups; and $R^2$ is halogen; $C_1$–$C_4$-alkyl, $C_1$–$C_4$-alkoxy, $C_2$–$C_6$-alkynyloxy or $C_5$–$C_{10}$-alkadienyloxy, where these groups may carry from one to five halogen atoms, one phenyl, phenoxy or phenylthio group or may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; benzyloxy where the aromatic groups may carry from one to five halogen atoms, or from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio provided that n is not 0 when m is 0; n is not 0 when m is 1 and $R^2$ denotes halogen in 4-position of the phenyl radical or when m is 2 and $R^2$ denotes halogen in 2- and 6-positions of the phenyl group.

4. A method of controlling arachnids, according to claim 1, wherein the arachnids are treated with an arachnicidally effective amount of an alpha-arylacrylic acid derivative of the formula I

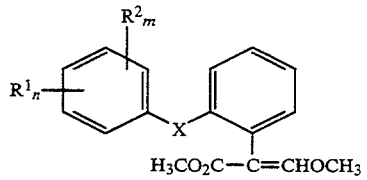

where
X is ethenylene;

n is 0 or 1;

m is 0, 1, 2, 3, or 4, and the groups $R_2$ may be different when m is 2, 3, or 4;

$R^1$ is cyano, $C_3$-$C_6$-cycloalkyl, or $C_2$-$C_6$-alkenyl, $R^2$ is halogen; $C_1$-$C_4$-alkyl, $C_1$-$C_4$-alkoxy, $C_2$-$C_6$-alkenyloxy or $C_5$-$C_{10}$-alkadienyloxy, where these groups may carry from one to five halogen atoms, one phenyl, phenoxy or phenylthio group or may carry from one to three of the following groups: $C_1$-$C_4$-alkoxy, $C_1$-$C_4$-haloalkoxy, $C_1$-$C_4$-alkylthio or $C_1$-$C_4$-haloalkylthio;

provided that n is not 0 when m is 0; n is not 0 when m is 1 and $R^2$ denotes halogen in 4-position of the phenyl radical or when m is 2 and $R^2$ denotes halogen in 2- and 6-positions of the phenyl group.

5. A method of controlling arachnids, according to claim 1, wherein the arachnids are treated with an arachnicidally effective amount of an alpha-arylacrylic acid derivative of the formula

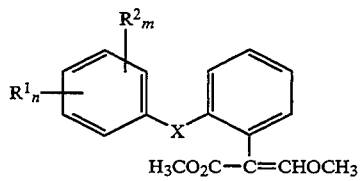

where

X is ethenylene;

n is 0 or 1;

m is 0, 1 or 2 and the radicals $R^2$ may be different when m is 2;

$R^1$ is $C_1$-$C_4$-haloalkyl, $C_1$-$C_4$-haloalkoxy, $C_3$-$C_6$-cycloalkyl, or $C_2$-$C_6$-alkenyl or $R^1$ together with $R^2$ in the ortho-position may form a 1, 3-butadiene-1, 4-diyl group, or a three-membered or four-membered chain consisting of carbon members and an oxygen member, where this chain may carry form one to three $C_1$-$C_4$-alkyl groups, and $R^2$ is halogen; $C_1$-$C_{10}$-alkyl, $C_1$-$C_6$-alkoxy where these groups may carry from one to five halogen atoms, or may carry from one to three of the following groups: $C_1$-$C_4$-alkoxy, $C_1$-$C_4$-haloalkoxy, $C_1$-$C_4$-alkylthio or $C_1$-$C_4$-haloalkylthio;

where the aromatic group may carry from one to five halogen atoms, or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio, provided that n is not 0 when m is 0; n is not 0 when m is 1 and $R^2$ denotes halogen in 4-position of the phenyl radical or when m is 2 and $R^2$ denotes halogen in 2- and 6-positions of the phenyl group.

6. A method of controlling arachnids, according to claim 1, wherein the arachnids are treated with an arachnicidally effective amount of an alpha-arylacrylic acid derivative of the formula I

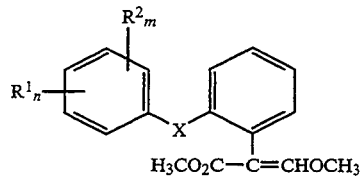

where

X is ethenylene;

n is 0 or 1;

m is 0, 1, or 2 and the groups $R^2$ may be different when m is 2;

$R^1$ is $C_3$-$C_8$-cycloalkyl, or $C_2$-$C_6$-alkenyl $R^2$ is halogen; $C_1$-$C_4$-alkyl or $C_1$-$C_4$-alkoxy where these groups may carry from one to five halogen atoms, or may carry from one to three of the following groups: $C_1$-$C_4$-haloalkoxy, $C_1$-$C_4$-alkylthio or $C_1$-$C_4$-haloalkylthio provided that n is not 0 when m is 0; n is not 0 when m is 1 and $R^2$ denotes halogen in 4-position of the phenyl radical or when m is 2 and $R_2$ denotes halogen in 2- and 6-positions of the phenyl group.

7. A method of controlling arachnids, according to claim 1, wherein the arachnids are treated with an arachnicidally effective amount of an alpha-aryl-acrylic acid derivative of the formula I A

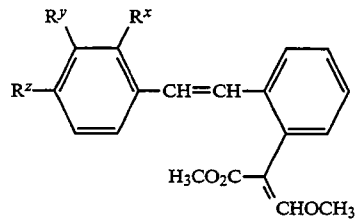

Wherein $R^x$ and $R^z$ denote hydrogen, halogen, $C_1$-$C_4$-alkyl, $C_1$-$C_4$-haloalkyl, $C_1$-$C_1$-$C_4$-alkoxy or $C_1$-$C_4$-haloalkoxy, $R^y$ denotes hydrogen, halogen, $C_1$-$C_4$-alkyl, $C_1$-$C_4$-haloalkyl, $C_1$-$C_4$-alkoxy or $C_1$-$C_4$-haloalkoxy, $C_3$-$C_6$-cycloalkyl, $C_3$-$C_6$-alkenyl or benzyloxy, or $R^y$ and $R^z$ together from a 1, 3-butadiene-1,4-diyl group or a $C_2$-$C_3$-alkylenoxy group, the latter being optionally substituted by one to three $C_1$-$C_4$-alkyl radicals, provided that at least one of the radicals $R^x$, $R^y$ and $R^z$ is not hydrogen.

8. A method according to claim 7, wherein the compounds IA are defined as follows:

$R^x$ and $R^z$ denote hydrogen, fluorine, chlorine, $C_1$-$C_4$-alkyl, $C_1$-$C_4$-haloalkyl, $C_1$-$C_4$-alkoxy or $C_1$-$C_4$-haloalkoxy, $R^y$ denotes hydrogen, fluorine, chlorine, bromine, $C_1$-$C_4$-haloalkyl, $C_1$-$C_4$-alkoxy, $C_1$-$C_2$-haloalkoxy, $C_3$-$C_6$-cycloalkyl, $C_3$-$C_6$-alkenyl or benzyl or $R^y$ and $R^z$ together form a 1,3-butadiene-1,4-diyl group or a $C_2$-alkylenoxy group, the latter being optionally substituted by one or two $C_1$-$C_2$-alkyl radicals.

9. A method according to claim 7, wherein the compounds IA are defined as follows:

$R^x$ and $R^z$ denote hydrogen, fluorine, chlorine, $C_1$-$C_2$-haloalkyl $C_1$-$C_4$-alkoxy or $C_1$-$C_4$-haloalkoxy, $R^y$ denotes hydrogen, fluorine, chlorine, $C_1$-$C_2$-haloalkyl, $C_1$-$C_2$-haloalkoxy or $C_3$-$C_6$-cycloalkyl.

* * * * *

UNITED STATES PATENT AND TRADEMARK OFFICE
CERTIFICATE OF CORRECTION

PATENT NO.: 5,356,931　　　　Page 1 of 3

DATED: October 18, 1994

INVENTOR(S): KIRSTGEN et al.

It is certified that error appears in the above-identified patent and that said Letters Patent is hereby corrected as shown below:

IN THE CLAIMS

Claim 1, column 28, line 49:
　　after "nitro" insert -- , --.

Claim 1, column 28, line 50:
　　before "haloalkyl" insert -- - --.

Claim 1, column 28, line 55:
　　after "$C_1$", first occurrence, insert -- - --.

Claim 1, column 29, line 31:
　　"R2" should read -- $R^2$ --.

Claim 2, column 29, line 54:
　　after "or", second occurrence, insert -- may carry --.

Claim 2, column 29, line 62:
　　before "or" insert -- group --.

Claim 2, column 29, line 60:
　　"form" should read -- from --.

Claim 2, column 29, line 63:
　　"$C_4$", third occurrence, should read -- $C_6$ --.

Claim 3, column 30, line 36:
　　"form" should read -- from --.

Claim 3, column 30, line 37:
　　"$C_4$", first occurrence, should read -- $C_{10}$ --.

UNITED STATES PATENT AND TRADEMARK OFFICE
CERTIFICATE OF CORRECTION

PATENT NO.: 5,356,931

DATED: October 18, 1994

INVENTOR(S): KIRSTGEN et al.

It is certified that error appears in the above-identified patent and that said Letters Patent is hereby corrected as shown below:

IN THE CLAIMS

Claim 3, column 30, line 37:
  "$C_4$", second occurrence, should read -- $C_6$ --.

Claim 4, column 31, line 4:
  "$C_6$", first occurrence, should read -- $C_8$ --.

Claim 5, column 31, line 39:
  "$C_6$" should read -- $C_8$ --.

Claim 5, column 31, line 46:
  "form" should read -- from --.

Claim 7, column 32, line 26:
  after "aryl" delete -- - --.

Claim 7, column 32, line 40:
  delete "$C_1$-", second occurrence.

Claim 8, column 32, line 53:
  "$C_4$", second occurrence, should read -- $C_2$ --.

UNITED STATES PATENT AND TRADEMARK OFFICE
CERTIFICATE OF CORRECTION

PATENT NO.: 5,356,931        Page 3 of 3

DATED: October 18, 1994

INVENTOR(S): KIRSTGEN et al.

It is certified that error appears in the above-identified patent and that said Letters Patent is hereby corrected as shown below:

IN THE CLAIMS

Claim 8, column 32, line 56:
 "$C_4$", first occurrence, should read -- $C_2$ --.

Claim 9, column 32, line 64:
 "$C_4$", both occurrences, should read -- $C_2$ --.

Signed and Sealed this

Fourth Day of April, 1995

Attest:

Attesting Officer

BRUCE LEHMAN

Commissioner of Patents and Trademarks